United States Patent [19]

Buchi et al.

[11] 3,974,225

[45] Aug. 10, 1976

[54] PROCESS FOR THE PREPARATION OF UNSATURATED ALDEHYDES

[75] Inventors: George H. Buchi; Hans Wuest, both of Cambridge, Mass.

[73] Assignee: Firmenich S.A., Geneva, Switzerland

[22] Filed: June 5, 1974

[21] Appl. No.: 476,430

[52] U.S. Cl.......................... 260/601 R; 260/465.1; 260/465.5 R; 260/465.9; 260/326.8
[51] Int. Cl.²......................................... C07C 45/21
[58] Field of Search ................................... 260/601

[56] References Cited
OTHER PUBLICATIONS

Fieser et al., "Reagents For Organic Synthesis," pp. 873–876.

Normant, "Advances in Organic Chemistry," vol. II, pp. 20–22 (1960).
Matsui et al., Chem. Abst., vol. 60, pp. 11889C.
Mander et al., J. Org. Chem., vol. 38, pp. 2915–2916.

*Primary Examiner*—James O. Thomas, Jr.
*Assistant Examiner*—James H. Reamer
*Attorney, Agent, or Firm*—Pennie & Edmonds

[57] ABSTRACT

Process for the preparation of unsaturated aldehydes, in particular $\gamma,\delta$-unsaturated aldehydes, which comprises reacting an amino-nitrile with a basic or a neutral agent.

The products obtained in accordance with the process of the invention are useful intermediates for the preparation of flavoring ingredients.

1 Claim, No Drawings

PROCESS FOR THE PREPARATION OF UNSATURATED ALDEHYDES

BACKGROUND OF THE INVENTION

The synthesis of poly-unsaturated aldehydes comprising four double bonds of formula

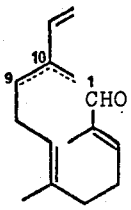

Ia,b wherein one of the double bonds is represented by the dotted lines, has been thoroughly studied in the past decade. In particular, α-sinensal of formula Ia, wherein the double bond represented by the dotted lines is located in the main chain, is a particularly useful flavoring ingredient. This compound is in fact a sesquiterpenic aldehyde which has been isolated from the oil of China orange (*Citrus sinensis*) [cf.: J. Org. Chem. 30, 1690 (1965), Tetrahedron Letters 295 (1966)] and which owing to its specific organoleptic properties has acquired a great value as flavouring agent for the aromatization of foodstuffs in general and beverages.

For the α-sinensal (Ia) and β-sinensal (Ib) whose structure is derived from cis or trans ocimene and from myrcene, respectively, the denomination α and β has been adopted by analogy with α- and β-farnesenes, respectively. In the past, a reverse system had been used (cf. Chem. Commun. 1968, 928), α in place of β and vice versa.

Although several processes for the preparation of α-sinensal have been reported in the chemical literature [cf. eg.: Helv. Chim. Acta 50, 2445 (1967); British patent specification No. 1,227,243] none of them has so far found a suitable industrial application. The difficulties encountered by the use of the described prior known processes are of different nature, ranging from poor availability of the starting material to contamination by metal catalyst of the product obtained. It is not surprising therefore that further investigations have been undertaken with the primary goal of synthetizing α-sinensal in a more economical and industrially convenient way.

THE INVENTION

It is an object of the present invention to provide a process for the preparation of γ,δ-unsaturated aldehydes of formula

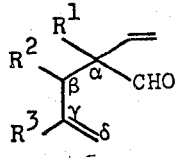

II wherein each of symbols $R^1$, $R^2$ and $R^3$, identical or different, represents an alkyl comprising from one to six carbon atoms, an alkenyl or an alkadienyl comprising from two to six carbon atoms, which process comprises treating an amino-nitrile of formula

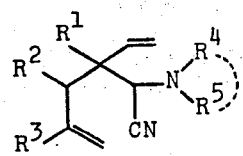

III wherein the symbols $R^1$, $R^2$ and $R^3$ have the meaning indicated above, and each one of symbols $R^4$ and $R^5$, identical or different, represents a lower alkyl radical, or $R^4$ together with $R^5$ and the nitrogen atom may constitute a heterocycloaliphatic ring as indicated by the dotted line,
with a basic or a neutral agent selected from the group consisting of alkali metal alkoxides or hydroxides and cyanide complexation agents.

This invention further relates to a process for the preparation of 2,6-dimethyl-2-vinyl-3-isopropenyl-octa-5,7-dienal which comprises reacting a poly-unsaturated amino-nitrile of formula

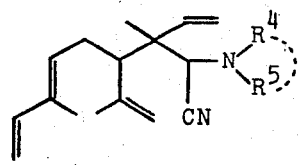

IIIa wherein the symbols $R^4$ and $R^5$ have the meaning given above, with a basic or a neutral agent selected from the group consisting of alkali metal alkoxides or hydroxides and cyanide complexation agents.

The invention also relates to the compounds of formula IIIa, which are new compounds. They represent useful industrial derivatives as key intermediates for the preparation of α-sinensal.

This invention finally relates to a process for the preparation of α-sinensal which comprises:
a. halogenating 3-methyl-penta-2,4-dienol,
b. reacting the obtained 3-methyl-penta-2,4-dien-1-yl bromide with mesityloxide in the presence of a strong basic agent,
c. reacting the obtained 3-isopropenyl-6-methyl-octa-5,7-dien- 2-one with vinyl-magnesium bromide,
d. halogenating the thus obtained 3,7-dimethyl-4-isopropenyl-nona-1,6,8-trien-3-ol,
e. treating the 3,7-dimethyl-4-isopropenyl-nona-2,6,8-trien-1-yl bromide obtained with an amino-cyanide of formula

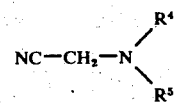

IV wherein $R^4$ and $R^5$ have the meaning indicated above, in the presence of a strong basic agent,
f. converting the amino-nitrile obtained into 2,6-dimethyl-2-vinyl-3-isopropenyl-octa-5,7-dienal by treating it with a basic or a neutral reagent selected from the group consisting of alkali metal alkoxides or hydroxides and cyanide complexation agents, and g. thermally treating said aldehyde to afford α-sinensal.

The hereinabove described process can be better visualized by the following reaction scheme.

Scheme

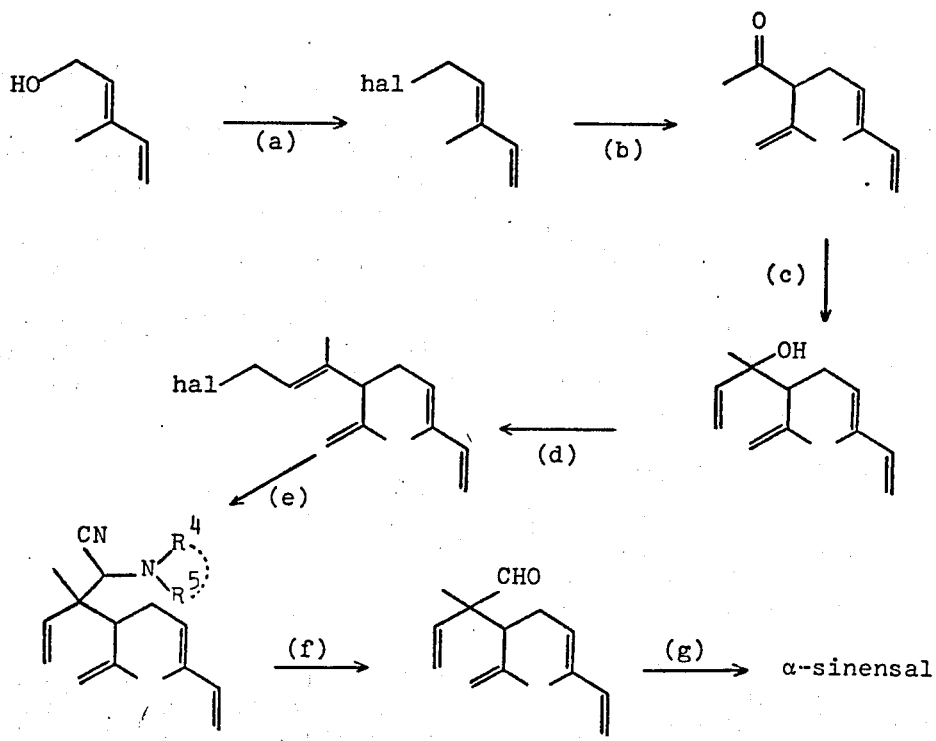

IIIa

PREFERRED EMBODIMENTS OF THE INVENTION

According to a preferred embodiment of one of the processes of the present invention the γ,δ-unsaturated aldehydes of formula II are prepared by treating an amino-nitrile of formula III with an alkali metal alkoxide or hydroxide. Suitable alkoxides include lithium, sodium and potassium methoxide and ethoxide. Sodium or potassium hydroxide in an ethanolic or aqueous-ethanolic solution are however preferred.

The reaction is preferably effected at the boiling temperature of the chosen solvent, usually ethanol or aqueous ethanol, or at a temperature lying in the vicinity of said boiling point.

Alternatively, the conversion of amino-nitrile III into its corresponding aldehyde II is carried out in the presence of a cyanide complexation agent, usually a salt of a d-block metal. Suitable cyanide complexation agents include salts of metals such as vanadium, chromium, manganese, iron, cobalt, nickel, copper, zinc, cadmium and mercury. Copper sulphate is preferred; however, any salt of metals able to form a stable cyano complex may be conveniently used [cf.: F. A. Cotton and G. Wilkinson, Advanced Inorganic Chemistry, second edition, Interscience Publ., New York (1966), p. 754–57. Said conversion is preferably carried out in an inert organic medium, in the presence, e.g., of a hydroxylic solvent such as methanol, ethanol and the like. Although the temperature at which the above said conversion was effected was not critical, it was observed that by carrying out the reaction at the boiling temperature of the chosen solvent, the reaction rate and the yields achieved were satisfactorily high.

The compounds of formula III, used as starting materials in the hereinabove described process, can be synthesized in accordance with the procedure illustrated in the above given reaction scheme.

Among the variety of the amino-nitriles represented by formula III, the compound of formula

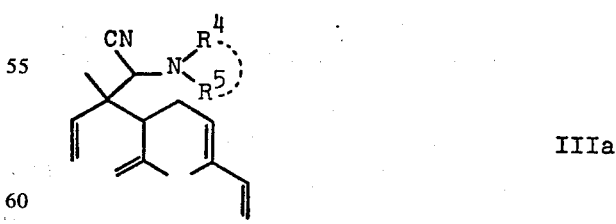

IIIa is particularly useful as intermediate in the preparation of α-sinensal. In the said formula each of the symbols $R^4$ and $R^5$, identical or different, represents a lower alkyl radical, or $R^4$ together with $R^5$ and the nitrogen atom may constitute a heterocycloaliphatic ring as indicated by the dotted line. Among the possible radicals, the following are of particular interest, methyl, ethyl, iso-propyl, —$(CH_2)_4$—.

This invention equally relates to the new nitrogen derivatives of formula IIIa.

As indicated above this invention equally provides a process for the preparation of α-sinensal by using as starting material 3-methyl-penta-2,3-dienol, a commercial product available from Fluka A. G., Buchs, St. Gall (Switzerland). This alcohol can equally be synthesized by one of the known methods, namely those described in Helv. Chim. Acta 49, 858 (1966), British patent specification No. 655,146 or U.S. Pat. No. 2,606,930.

In accordance with preferred embodiments of the process hereinabove defined the first reaction step, which merely consists in a halogenation of 3-methyl-penta-2,4-dienol, can be effected by one of the reactants commonly used for converting a hydroxy derivative into an alkyl halide [cf. e.g.: R. B. Wagner and H. D. Zook, Synthetic Organic Chemistry, New York (1953), p. 88 and ff.]. To this effect phosphorous halides in the presence of a tertiary amine, such as pyridine, dimethylaniline or collidine, are preferred. Phosphorous tribromide is most conveniently used.

The subsequent addition of mesityloxide is effected in the presence of a strong basic agent. Suitable basic agents include an alkali metal hydride or amide, namely sodium hydride or sodium amide. This latter is preferred. The reaction proceeds more favorably at a temperature ranging from about −70° to −30°C, preferably at about −30°. Optionally the reaction with sodium amide can be carried out in liquid ammonia containing traces of water. It has been observed in fact that the best yields in 3-isopropenyl-6-methyl-octa-5,7-dien-2-one were achieved by the use of a medium constituted by wet liquid ammonia.

The subsequent addition of vinylmagnesium bromide is effected in accordance with the usual techniques of the Grignard type reactions. Preferably, the reaction was carried out by using an excess of reactant in an inert organic solvent, preferably tetrahydrofuran. The vinylmagnesium bromide can be prepared according to Org. Synth. IV, p. 258.

The conversion of the obtained 3,7-dimethyl-4-isopropenyl-nona-1,6,8-trien-3-ol into 3,7-dimethyl-4-isopropenyl-nona-2,6,8-trien-1-yl bromide is effected by means of coventional halogenation reagents such as phosphorous tribromide. This halogenation is carried out in an inert organic solvent, preferably an ether, at a temperature comprised in between about −5° and 20°C, preferably in between 0° and +20°C.

The formation of the corresponding amino-nitrile is promoted by an amino-cyanide of formula IV. Suitable reagents IV include N-cyanomethyl-dimethylamine, N-cyanomethyl-diethylamine, N-cyanomethyldiisopropylamine and N-cyanomethyl-pyrrolidine (NCMP). These compounds can be synthesized according to known methods [cf. e.g.: Liebigs Ann. Chem. 279, 39 (1894); Bull. Soc. Chim. Fr. 383 (1960)].

In a typical experiment 3,7-dimethyl-4-isopropenyl-nona-2,6,8-trien-1-yl bromide was dissolved in anhydrous tetrahydrofuran and N-cyanomethyl-dimethylamine was added thereto at room temperature. Potassium tert-butoxide in tetrahydrofuran solution was then added to the reaction mixture at −30°C in a nitrogen atmosphere. By subsequent treatment with water followed by extraction with ether the desired nitrile was isolated in excellent yields.

Potassium tert-butoxide can be replaced with sodium or potassium methoxide or ethoxide. Analogous results were thus observed; however, the yields achieved were inferior.

The subsequent reaction step consists in the conversion of the above obtained amino-nitrile into its corresponding aldehyde. This reaction can be effected in accordance with the general procedure above described for the conversion of compounds of formula III into the γ,δ-unsaturated carbonyl derivatives of formula II. The same reaction conditions successfully apply here.

Finally, the formation of α-sinensal proceeds by thermal treatment of the obtained 2,6-dimethyl-2-vinyl-3-isopropenyl-octa-5,7-dienal in the presence of a basic or neutral agent. Suitable neutral agents include alkali metal salts such as sodium or potassium carbonate or bicarbonate. Suitable basic agents include alkali metal salts such as sodium or potassium carbonate or bicarbonate and strong base anion exchange resins (e.g., REXYN 201 available from Fisher Scientific Co.) or organic bases such as tertiary amines, e.g, quinoline. The reaction is effected in an inert organic solvent whose boiling point at atmospheric pressure is preferably higher than 100°C. Aliphatic, cycloaliphatic or aromatic hydrocarbons can be successfully used to this end. High boiling alcohols, such as n-butanol, are equally effective. Of course, the choice of the medium is dependent on the particular pressure at which the reaction is carried out.

Low boiling solvents may equally provide useful media whenever the reaction is effected at a pressure higher than the atmospheric pressure. For economical reasons xylene is preferred. It will be appreciated that the reaction time may vary within a wide range and depends particularly on the temperature chosen for carrying out the rearrangement. In a typical experiment 2,6-dimethyl-2-vinyl-3-isopropenyl-octa-5,7-dienal in xylene was heated at reflux for 40 min. under nitrogen. Sodium carbonate and methanol were added to the reaction mixture and the reaction mixture was further refluxed for 18 h while stirring. After dilution with pentane and drying over anhydrous sodium sulphate, the mixture was distilled to yield α-sinensal.

The invention is illustrated in a more detailed manner but not limited by the following example wherein the temperatures are indicated in degrees centigrade and the abbreviations have the meaning common in the art.

EXAMPLE

The following spectrometers were used:
NMR: Varian T-60 (CCl$_4$, (CH$_3$)$_4$Si as internal standard);
IR: Hitachi-Perkin Elmer Mod. 247 (CHCl$_3$);
UV: Cary Model 14 (EtOH);
MS: Hitachi-Perkin Elmer RMU-60
GLC: The gas chromatography analysis were performed on an F and M 720 instrument using silicon rubber gum SE-30 and CARBOWAX columns.

The melting points were determined on a hot stage microscope and are uncorrected.

a. 3-Methyl-penta-2,4-dien-1-yl Bromide 89.5 g (0.33 M) of phosphorous tribromide in 60 ml of diethylether were added at 5°–10° to a mixture of 80 g (0.82 M) of trans-methyl-3-penta-2,4-dienol (Fluka A. G., Buchs/St. Gall, Switzerland), 3.2 g (0.04 M) of pyridine and 200 ml of dry ether. Stirring was continued for 15 min. at 5°, then ice-water was added. The organic layer was separated, washed with water, 5% aqueous sodium bicarbonate, a saturated solution of sodium chloride and finally dried over sodium sulphate and concentrated. A subsequent distillation of the obtained residue yielded 111.4 g (84%) of the desired alkadienyl bromide; b.p. 45°/10 Torr.

IR: 1820, 1600, 985, 905 cm$^{-1}$
NMR: 1.85 (3H, s); 4.05 (2H, d, J=8.5 Hz); 5.1 (1H, d, J=10 Hz); 5.3 (1H, d, J=18 Hz); 5.75 (1H, t, J=8.5 Hz); 6.35 (1H, d of d, J=10 and 18 Hz) δ ppm
UV: 247 nm (ε=17,800)
MS: m/e: 162 (29), 160 (29), 81 (100), 79 (92).

b. 3-Isopropenyl-6-methyl-octa-5,7-dien-2-one

Sodium amide was prepared from 4.7 g (0.2 g-atom) of sodium in 150 ml of liquid ammonia in the presence of a few crystals of ferric nitrate. The ammonia was not dried and no precautions were taken to exclude moisture. 24 g (0.24 M) of mesityloxide were added to the stirred suspension at reflux (−33°) over a period of 10 min. Stirring was continued for 10 min., then 34 g (0.2 M) of the bromide prepared according to the method given sub. (a), was added to the reaction mixture within 15 min. at reflux. The ammonia was allowed to evaporate and was gradually replaced with ether. After thetemperature had the temperature −10° the mixture was poured into cold aqueous ammonium chloride. The organic layer was separated, washed with water, dried over sodium sulphate and concentrated. A distillation of the obtained residue gave 31.4 g (88%) of the desired dienone whose b.p. was 60°/0.1 Torr;

IR: 1710, 1650, 1610, 1360, 990, 900 cm$^{-1}$
NMR: 1.65 (3H, s with fine splittings); 1.75 (3H, s); 2.0 (3H, s); 2.1–2.9 (2H, m); 3.15 (1H, t, J=7.5 Hz); 4.7–5.5 (5H, m); 6.25 (1H, d of d, J=10 and 17 Hz) δ ppm
UV: 230 nm (ε=23,700)
MS: m/e: 178 (6), 135 (71), 81 (100), 43 (76).

c. 3,7-Dimethyl-4-isopropenyl-nona-1,6,8-trien-3-ol

A solution of 48 g (0.27 M) of the dienone prepared according to the method indicated sub (b), in 50 ml of tetrahydrofuran was added dropwise at 15°–20° to a Grignard reagent prepared from 36 g (1.5 g-atom) of 40 mesh magnesium powder and 65 g (0.6 M) of vinyl bromide in 250 ml of tetrahydrofuran. After 30 min. at room temperature the mixture was poured into a cold ammonium chloride aqueous solution, extracted with ether, washed with water, dried over Na$_2$SO$_4$, concentrated and distilled to yield 46.8 g (84%) of the desired trienol with b.p. 67°/0.1 Torr;

IR: 3640, 3570, 1665, 1610, 990, 920, 895 cm$^{-1}$
NMR: 1.2 (3H, s); 1.5 (1H, s); 1.7 (6H, s); 1.8–2.5 (3H, m); 4.7–5.5 (7H, m); 5.9 (1H, d of d, J=10 and 17 Hz); 6.25 (1H, d of d, J=10 and 17 Hz) δ ppm
UV: 232 nm (ε=25,800)
MS: m/e: 206 (4), 92 (93), 81 (94), 71 (100).

d. 3,7-Dimethyl-4-isopropenyl-nona-2,6,8-trien-1-yl Bromide 16.3 g (0.06 M) of phosphorous tribromide in 40 ml of ether were added at 0°–5° to a mixture of 30.9 g (0.15 M) of the trienol prepared sub (c), 0.8 g (0.01 M) of pyridine and 200 ml of anhydrous ether. The mixture was allowed to warm up to room temperature and, after stirring for 1 h at 25°, it was poured onto ice. The organic layer was separated, washed with a cold concentrated solution of NaCl containing sodium bicarbonate, dried over Na$_2$SO$_4$ and concentrated at 20°/10 Torr to give 39.2 g of the desired bromide.

IR: 1640, 1610, 990, 895 cm$^{-1}$
NMR: 1.65 (6H, s); 1.75 (3H, s); 2.1–2.8 (3H, m); 3.95 (2H, d, J=8 Hz); 4.7–5.8 (6H, m); 6.3 (1H, d of d, J=10 and 18 Hz) δ ppm.

e. 3,7-Dimethyl-4-isopropenyl-3-(N-cyanomethyldimethylamino)-nona-1,6,8-triene

The N-cyanomethyldimethylamine was prepared in accordance with the procedure described in Liebigs Ann. Chem. 279, 39 (1894) as follows:

81 g (1 M) of 70% aqueous glycolonitrile (Fluka A. G., Buchs/St. Gall, Switzerland) was added dropwise at 45° to 112 g (1 M) of aqueous 40% dimethylamine.

The mixture was saturated with sodium chloride and extracted several times with ether. The combined extracts were dried over K$_2$CO$_3$, distilled at 50 Torr and redistilled at atmospheric pressure to give 54 g (64%) of N-cyanomethyldimethylamine, b.p. 137°; IR: 2240 cm$^{-1}$; NMR: 2.15 (6H, s); 3.4 (2H, s) δ ppm. 12.6 g (0.15 M) of N-cyanomethyldimethylamine was added to 39.2 g of the crude bromide prepared in accordance with the method described sub (d) in 150 ml of anhydrous tetrahydrofuran. The temperature was kept below 30° by occasional cooling. After 16 h at room temperature a solution of 16.8 g (0.15 M) of potassium tert-butoxide in 80 ml of tetrahydrofuran was added at −30° under nitrogen. After completion of the addition the cold (−30°) reaction mixture was poured into water and extracted with ether.

The organic layer was washed with saturated aqueous sodium chloride, dried over Na$_2$SO$_4$ and concentrated to yield 38.7 g of the desired amino-nitrile.

IR: 2240, 1640, 1610, 990, 925 and 900 cm$^{-1}$.

f. 2,6-Dimethyl-2-vinyl-3-isopropenyl-octa-5,7-dienal

A stirred mixture of 38.7 g of the crude amino-nitrile prepared according to the procedure described sub (e), 300 ml of aqueous 2N NaOH and 150 ml of 95% ethanol was heated at reflux for 90 min. under nitrogen. Extraction with ether, washing with water, drying over Na$_2$SO$_4$ and concentrating were followed by distillation which gave 21.8 g of the desired dienal, b.p. 72°-6°/0.15 Torr.

An analytical sample purified by column chromatography on silica gel using hexane with 2% of ethyl acetate, had b.p. 70°/0.1 Torr.

IR: 2720, 1720, 1640, 1610, 990, 920, 900 cm$^{-1}$
NMR: 1.15 (2H, s); 1.2 (1H, s); 1.7 (3H, s); 1.75 (3H, s); 1.9–2.7 (3H, m); 4.6–6.6 (9H, m); 9.35 (s); 9.4 (s) δ ppm.

Integration of the signals at 9.35 and 9.4 indicated the presence of two diastereoisomers in a ratio of 6:4.

UV: 232 nm (ε=25,200)
MS: m/e: 218 (20), 81 (83), 55 (100), 44 (94).

Alternatively, 5.0 g (18.4 mM) of the amino-nitrile prepared according to letter (e), 3.5 g (14 mM) of CuSO$_4$·5H$_2$O and 50 ml of 95% methanol were heated under stirring at reflux for 5 min. in a nitrogen atmosphere. After removal of the solvent in vacuo, ether was added and the mixture was stirred for 15 min. at room temperature, then filtered and concentrated. A distillation gave 3.27 g (82%) of the desired aldehyde, b.p. 65°10.1 Torr.

g. α-Sinensal 21.8 g of the dienal prepared sub (*f*) in 150 ml of xylene was heated at reflux for 40 min. under nitrogen. The solution was cooled, and 5 g of anhydrous sodium carbonate and 150 ml of methanol were added to it, while stirring was carried on for 18 h at reflux. The mixture was diluted with pentane, washed with water, dried over $Na_2SO_4$, concentrated and distilled to give 14.4 g of α-sinensal, b.p. 84–6°/0.1 Torr. The obtained product was further purified by fractional distillation on a 30 cm Vigreux column and had b.p. 82°/0.1 Torr.

IR: 2740, 1680, 1640, 1610, 990 and 895 $cm^{-1}$ NMR: 1.7 (9H, broad s); 1.9–2.6 (4H, m); 2.8 (2H, t, J=7 Hz); 4.7–5.5 (4H, m); 6.0–6.5 (2H, m); 9.3 (1H, s) δ ppm UV: 232 nm (ε=40,900)

MS: m/e: 218 (4), 55 (50), 49 (53), 44 (100).

The 2,4-dinitrophenylhydrazone had m.p. 98°–100.5° pure and m.p. 98°–101° when admixed with an authentic sample (m.p. 100°–102.5°).

Similar results were achieved when using the following reactants:

a. same as described, but $Na_2CO_3$ was replaced by a strong base anion exchange resin,
b. n-butanol and $Na_2CO_3$ at reflux for 6 h,
c. quinoline, 10 min. at reflux.

What we claim is:

1. A process for the preparation of α-sinensal which comprises:
   a. brominating 3-methyl-penta-2,4-dienol,
   b. reacting the obtained 3-methyl-penta-2,4-dien-1-yl bromide with mesityloxide at a temperature of from about −70°C to about −30°C in the presence of an alkali metal hydride or alkali metal amine,
   c. reacting the obtained 3-isopropenyl-6-methyl-octa-5,7-dien-2-one with vinyl-magnesium bromide,
   d. brominating the thus obtained 3,7-dimethyl-4-isopropenyl-3-nona-1,6,8-trien-3-ol at a temperature from about −5°C to about +20°C and in the presence of an inert organic solvent
   e. treating the 3,7-dimethyl-4-isopropenyl-nona-2,6,8-trien-1-yl bromide obtained with an amino-cyanide of formula

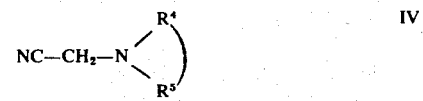

wherein each one of the symbols $R^4$ and $R^5$, identical or different, represents a lower alkyl radical, or $R^4$ together with $R^5$ and the nitrogen atom may constitute a heterocycloaliphatic ring as indicated by the dotted line, and subsequently adding to the reaction mixture a strong basic agent selected from the group consisting of potassium tert-butoxide, sodium ethoxide, potassium methoxide and potassium ethoxide,
   f. converting the amino-nitrile obtained into 2,6-dimethyl-2-vinyl-3-isopropenyl-octa-5,7-dienal by treating it with a basic or a neutral reagent selected from the group consisting of alkali metal alkoxides or hydroxides and cyanide complexation agents, and in the presence of an inert organic solvent, and
   g. thermally treating said aldehyde at a temperature above about 100°C in the presence of a basic or a neutral agent selected from the group consisting of an alkali metal salt, a strong base anion exchange resin and a tertiary amine in an inert organic solvent.

* * * * *

UNITED STATES PATENT AND TRADEMARK OFFICE
CERTIFICATE OF CORRECTION

PATENT NO. : 3,974,225
DATED : August 10, 1976
INVENTOR(S) : George H. Buchi et al.

It is certified that error appears in the above-identified patent and that said Letters Patent are hereby corrected as shown below:

Column 2, line 60 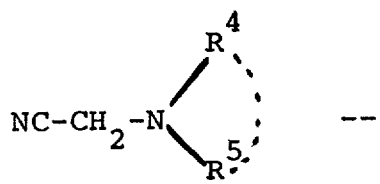 should be --

NC-CH$_2$-N$\begin{smallmatrix}R^4\\R^5\end{smallmatrix}$  --

Column 3, lines 66-67 "p. 754-57" should be --pp. 754-5]--

Column 5, line 10 "655,146" should be --665,146--

Column 7, line 25 "the temperature had the temperature -10°" should be -- the temperature had reached -10°--

Column 8, line 68 "65°10.1 Torr" should be --65°/0.1 Torr--

Column 9, line 14 "cm$^{-1}$ NMR: " should be --cm$^{-1}$
                                (new line)NMR:--

Column 10, Formula " 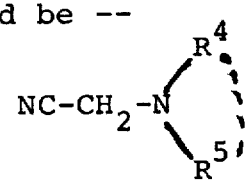 " should be -- 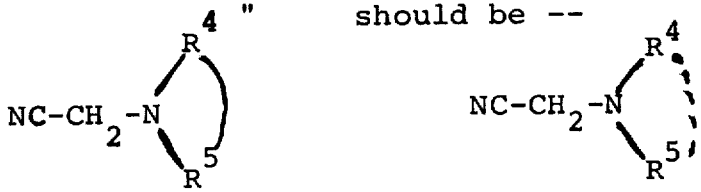

Signed and Sealed this

Sixteenth Day of November 1976

[SEAL]

Attest:

RUTH C. MASON
*Attesting Officer*

C. MARSHALL DANN
*Commissioner of Patents and Trademarks*